United States Patent [19]

Alink

[11] Patent Number: 4,477,674

[45] Date of Patent: Oct. 16, 1984

[54] PREPARATION OF DIHYDROTHIAZOLES

[75] Inventor: Bernardus A. O. Alink, St. Louis, Mo.

[73] Assignee: Petrolite Corporation, St. Louis, Mo.

[21] Appl. No.: 472,332

[22] Filed: Mar. 4, 1983

Related U.S. Application Data

[62] Division of Ser. No. 112,506, Jan. 16, 1980, abandoned.

[51] Int. Cl.$^3$ .......................................... C07D 233/04
[52] U.S. Cl. .................................... 548/146; 424/270
[58] Field of Search ......................... 548/146; 424/270

[56] References Cited

U.S. PATENT DOCUMENTS

| | | | |
|---|---|---|---|
| 2,886,571 | 5/1959 | Schade et al. | 260/306.7 |
| 3,004,981 | 10/1961 | Asinger et al. | 548/146 |
| 3,700,683 | 10/1972 | Asinger et al. | 548/146 |
| 4,153,606 | 5/1979 | Scherberich | 548/146 |

*Primary Examiner*—Nicholas S. Rizzo
*Attorney, Agent, or Firm*—Sidney B. Ring; Leon Zitver

[57] ABSTRACT

This invention relates to dihydrothiazoles and to the preparation thereof by reacting aza-alkylene-dienes with sulfur.

2 Claims, No Drawings

PREPARATION OF DIHYDROTHIAZOLES

This is a division of application Ser. No. 112,506, filed Jan. 16, 1980 now abandoned.

In U.S. Pat. No. 4,106,904 there is described the reaction of aldehyde with ammonia. Where the alpha carbon of the aldehyde is unsubstituted, a cyclic compound is formed in accord with the following equation:

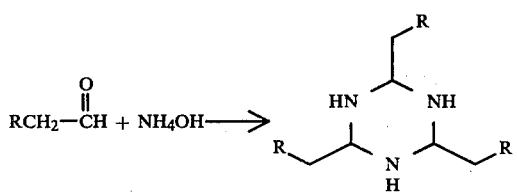

However, as disclosed by Hasek et al J Org Chem 26, 1822 (1961) where the alpha carbon is substituted non-cyclic, compounds are formed in accord with the following reactions:

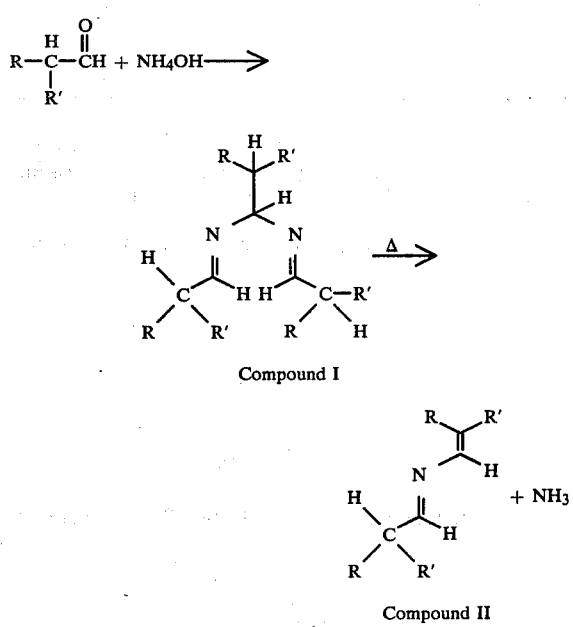

I have now discovered that where Compounds I and/or II are reacted with sulfur, dihydrothiazoles are formed.

This is illustrated by the following reaction:

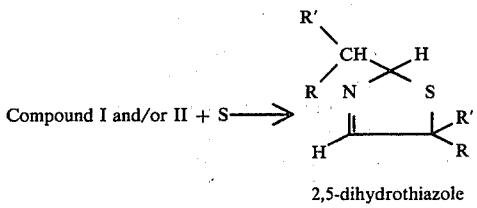

The reaction is carried out by heating a mixture of Compound I or II and elemental sulfur in stoichiometric amounts at temperatures from 40°–160° C. for 1–24 hrs. Solvents which do not interfere with the reaction may be used but are not necessary.

R and R', which are the moieties of the aldehyde reactant, may be any group which does not interfere with the reaction such as alkyl, cycloalkyl, aryl, aralkyl, alkarylalkyl, etc., but preferably alkyl.

Thus, in the dihydrothiazoles of this invention of the formula

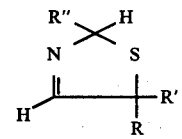

R'' is a branched hydrocarbon, preferably branched alkyl such as

where R and R' have the same meaning as the R and R' groups at position 5.

The following examples are presented for purposes of illustration and not of limitation.

EXAMPLE 1

3,7-Diethyl-5-azanona-3,5-diene

To a sample of 250 grams of 28% ammonium hydroxide was added 215 grams of 2-ethylbutyraldehyde and the heterogeneous mixture was stirred for 18 hours at ambient temperature. The resulting organic layer was separated, and after drying, slowly distilled at atmospheric pressure to yield 148.8 grams of 3,7-diethyl-5-azanona-3,5-diene.

Mass spectrum m/e=181. $^{13}$C nuclear magnetic resonance spectrum, solvent CDCl$_3$, ref. TMS.

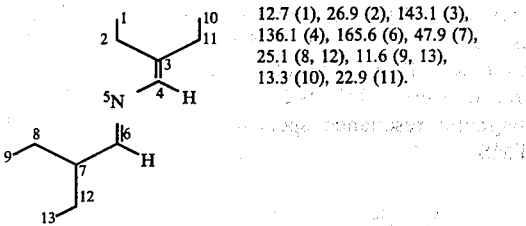

12.7 (1), 26.9 (2), 143.1 (3), 136.1 (4), 165.6 (6), 47.9 (7), 25.1 (8, 12), 11.6 (9, 13), 13.3 (10), 22.9 (11).

EXAMPLE 2

2,5-Dihydro-5,5-diethyl-2-(1-ethylpropyl) thiazole

A sample of 147.8 grams of 3,7-diethyl-5-azanona-3,5-diene, prepared as described in example 1 and 26 grams of elemental sulfur were heated at 150° C. for 19 hours. The resulting product was distilled under diminished pressure and the fraction b.$_{25}$ 145°–150° C., was identified as 128 grams of 2,5-dihydro-5,5-diethyl-2-(1-ethylpropyl) thiazole.

Mass spectrum m/e=213, $^{13}$C nuclear magnetic resonance spectrum, solvent CDCl$_3$, ref TMS.

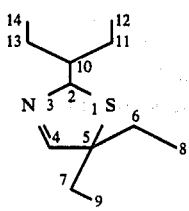

87.0 (2), 166.6 (4), 74.4 (5),
24.9 (6), 32.2 (7), 9.4 (8),
10.1 (9), 47.9 (10), 23.4 (11),
11.2 (12) 22.7 (13), 10.8 (14).

EXAMPLE 3

2,6-Dimethyl-4-azahepta-2,4-diene

To 1400 grams of a 28% solution of ammonium hydroxide was added with stirring over a 4 hour period 1400 grams of isobutyraldehyde while a reaction temperature of 22°–47° was maintained. After completion of the addition stirring was continued for 18 more hours. The resulting organic layer was refluxed under azeotropical conditions until ammonia evolution ceased (14 hours). The resulting 1137.8 grams of product was identified as 2,6-dimethyl-4-azahepta-2,4-diene.

Mass spectrum m/e=125. $^{13}$C nuclear magnetic resonance spectrum, solvent CDCl$_3$, reference TMS.

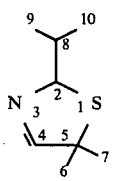

22.5 (1), 132.2 (2), 137.3 (3),
166.0 (5), 34.0 (6), 19.5 (7, 8),
17.7 (9).

EXAMPLE 4

2,5-Dihydro-5,5-dimethyl-2-(1-methylethyl) thiazole

A mixture of 364.9 grams of 2,6-dimethyl-4-azahepta-2,4-diene prepared as described in example 2 and 93.6 grams of elemental sulfur was heated for 6 hours at 145° C. The resulting product was distilled under diminished pressure and the fraction b.$_{25}$ 91°–93° C. was identified as 280 grams of 2,5-dihydro-5,5-dimethyl-2-(1-methylethyl) thiazole. chemical ionization mass spectroscopy m/e=157, 142, 124, 114, 90, 86. $^{13}$C nuclear magnetic resonance spectrum. Solvent CDCl$_3$, Ref. TMS.

90.4 (2), 167.7 (4), 63.1 (5),
29.4 (6), 29.0 (7), 34.5 (8),
18.2 (9), 19.6 (10).

Using the procedures of examples 2 and 4, several other substituted 2,5-dihydrothiazoles were prepared from the corresponding unsaturated imines. The results are summarized in Table I.

TABLE I

| Example No. | Starting imine | Product |
|---|---|---|
| 5 | 4,9-Diethyl-7-azatrideca-5,7-diene | 2,5-Dihydro-5-butyl-5-ethyl-2(1-ethylpentyl)thiazole |
| 6 | 3,7-Dimethyl-5azanona-3,5-diene | 2,5-Dihydro-5-ethyl-5-methyl 2-(1-methylpropyl)thiazole |

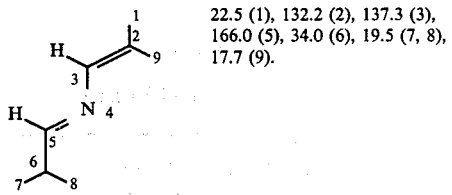

The compositions of this invention have a wide variety of uses. For example, they are useful as corrosion inhibitors, antioxidants, fuel oil additives, etc.

I claim:

1. A process of preparing a dihydrothiazole of the formula

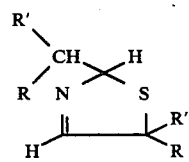

which comprises reacting a corresponding reactant of the formula

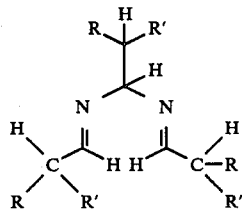

where R and R' are selected from the group consisting of alkyl, cycloalkyl, aryl, aralkyl and alkarylalkyl, with sulfur in stoichiometric amounts at temperatures of from 40°–160° C. for 1–24 hours.

2. The process of claim 1 where R and R' are alkyl.

* * * * *